(12) United States Patent
Saied et al.

(10) Patent No.: US 7,637,165 B2
(45) Date of Patent: Dec. 29, 2009

(54) PRESSURE MEASURING MANOMETER WITH ALIGNMENT SPUR

(75) Inventors: Abdolreza Saied, Carmichael, CA (US); James I-Che Lee, Sacramento, CA (US)

(73) Assignee: VORTRAN Medical Technology 1, Inc., Sacramento, CA (US)

( * ) Notice: Subject to any disclaimer, the term of this patent is extended or adjusted under 35 U.S.C. 154(b) by 44 days.

(21) Appl. No.: 12/009,104

(22) Filed: Jan. 15, 2008

(65) Prior Publication Data

US 2009/0090188 A1    Apr. 9, 2009

Related U.S. Application Data

(60) Provisional application No. 60/885,177, filed on Jan. 16, 2007.

(51) Int. Cl.
*G01L 13/02* (2006.01)
(52) U.S. Cl. ........................................................ 73/716
(58) Field of Classification Search ................ 73/715, 73/756, 736
See application file for complete search history.

(56) References Cited

U.S. PATENT DOCUMENTS

| | | | |
|---|---|---|---|
| 2,655,037 A * | 10/1953 | Gess | 73/862.583 |
| 2,850,901 A * | 9/1958 | Proctor | 73/736 |
| 4,058,016 A | 11/1977 | Schwartz | |
| 4,063,459 A | 12/1977 | Prell | |
| 4,107,996 A | 8/1978 | Hollingsworth | |
| 5,557,049 A | 9/1996 | Ratner | |
| 6,120,458 A | 9/2000 | Lia et al. | |
| 6,619,128 B1 | 9/2003 | Hui | |
| 6,637,272 B1 * | 10/2003 | Bariere | 73/715 |
| 7,051,594 B1 | 5/2006 | Aziz | |
| 7,051,596 B1 | 5/2006 | Lau et al. | |
| 7,357,033 B2 * | 4/2008 | Lau et al. | 73/736 |
| 2006/0118123 A1 | 6/2006 | Quinn et al. | |
| 2006/0156823 A1* | 7/2006 | Lau et al. | 73/716 |

\* cited by examiner

*Primary Examiner*—Andre J Allen (57) ABSTRACT

A measuring device for detecting and indicating changes in fluid pressure of a test environment relative to ambient fluid conditions, wherein the measuring device includes a linear gear rack having an alignment spur, an indicator needle associated pinion gear, calibrated indicia for visual measure of a pressure change event, and a deflectable diaphragm element. The alignment spur acts upon the pinion gear by maintaining close relationship of the linear gear rack and the needle associated pinion gear and counteracts torque and off-center forces created by the linear rack gear upon deflection of the deflectable diaphragm, thus providing improved resolution of small pressure changes and increased accuracy of measurement as the measuring device operates through a cycling period.

4 Claims, 10 Drawing Sheets

PRESSURE MEASURING MANOMETER WITH ALIGNMENT SPUR

PARENT CASE TEXT

This application claims the benefit under 35 U.S.C. 119(e) of U.S. provisional application Ser. No. 60/885,177 filed Jan. 16, 2007, which is incorporated by reference herein in its entirety.

BACKGROUND

Measurement of pressure in fluidic environments, which can include either gaseous or liquid conditions, has been addressed by numerous ways and means. Of particular interest in measuring fluidic environments through the years has been the use of mechanical devices which react to a difference between an ambient environmental or control pressure and a closed or otherwise constrained test environmental pressure. Mechanical devices are advantageous in that such equipment is conducive to mass production, offers increased durability and consistency in performance, and can be readily applied to various pressure measurement applications.

Adaptation of mechanical pressure measurement devices is of particular importance when dealing with a gaseous system which is either adversely affected by pressure extremes or it is critical to maintain a gaseous system within required upper and lower levels. In such sensitive applications, the mechanical device must be responsive to small changes in pressure and readily/repeatedly indicate the pressure measurements of the gaseous environment in a clear and concise way. Further, where it is necessary to determine sudden changes in pressure, the device must be capable of indicating such changes immediately and accurately at the time as such occurs.

One system wherein sudden, small and repeated pressure changes are significant in interpreting overall performance attributes is the respiratory system of a human patient, wherein the measuring device is used in the form of a pressure measuring manometer. Prior pressure measuring manometers have utilized a number of different mechanical actions to indicate respiratory pressure measurements with differing levels of efficiency and effectiveness. U.S. Pat. No. 5,535,740 to Baghaee-Rezaee utilizes a bellow-type pressure gauge utilizing a bifurcated port to measure either a positive or negative pressure change. U.S. Pat. No. 5,557,049 to Ratner utilizes a diaphragm associated with a spiral shaped actuator stem and a top-down visible flat radial dial indicator. U.S. Pat. No. 5,606,131 to Pope employs a sliding, spring biased piston enclosed in a tube having pressure measurement indicia printed thereon.

The aforementioned pressure manometers each offer a means for displaying pressure changes in a respiratory circuit or ventilation environment. However, there remains an unmet need for a pressure manometer for measuring patient lung performance that is simple to use, sensitive, efficient, accurate and reliable over a continuous period of cycling.

SUMMARY OF THE INVENTION

The present invention comprises a pressure measuring manometer configured to show positive and/or negative changes in pressure of a test fluidic environment relative to an ambient fluid environment. The pressure measuring manometer has a linear gear rack that moves in response to motion of a diaphragm as the diaphragm deflects relative to cyclic increase and decrease in pressure. A pinion gear is engaged to the linear gear rack such that as the linear gear rack moves back and forth in a linear orientation, the associated pinion gear converts the linear motion into a corresponding rotational moment. An indicator needle associated with the pinion gear converts the rotational moment of the pinion gear into deflection of the needle, with the relative pressure change being read by interpreting the position of the indication needle relative to overlaid calibrated measurement indicia. An included alignment spur extends directly opposite the linear rack gear and is located proximal to the pinion gear. The alignment spur is in close proximity to the pinion gear and performs several important functions, including: maintaining the pinion gear in close physical relationship to the linear gear rack thus insuring uniform and precise movement of the linear rack relative to deflection of the diaphragm; low mass to enable rapid response to small changes in pressure; counteracting torque created by the action of the linear gear rack maintaining a perpendicular orientation of the linear gear rack to the diaphragm element; and, overcoming backlash of the indicator needle relative to the measurement indicia. A biasing spring may be included within the device so as to act upon the linear gear rack and the indicating needle associated pinion to establish a zero-state and provide resistance to movement of the indicator until energy is imparted upon the diaphragm element by a change in pressure.

An embodiment of the pressure measuring manometer in accordance with the present invention is used to measure pressure in the continuously changing gaseous environment of a human respiratory system. Pressure changes through the continuous exhalation and inhalation by the patient imparts energy into the diaphragm element, which is then repeatedly translated by the linear gear rack, alignment spur and pinion gear into corresponding measures of pressure created by each of the patient's own momentary respiration events. In order to be of value to a medical clinician, such a pressure measuring manometer should be minimally responsive to a an adult patient respiratory rate within a normal range of up to 40 cycles per minute, and a minimum useful lifecycle of the pressure measuring manometer of at least 3000 continuous cycles at an average rate of 10 cycles per minute.

A further embodiment of the present invention is a pressure measuring manometer that acts in conjunction with a patient respiratory ventilation system so as to indicate the internal pressure therein. The manometer has a pressure chamber coupled to the ventilation via an inlet port, wherein the diaphragm element is disposed within the pressure chamber such that changes in pressure within the pressure chamber causes deflection of the diaphragm element. A linear gear rack is coupled to the diaphragm such that motion of the diaphragm element is translated as linear motion of the linear gear rack. The linear gear rack has a plurality of adjacent gear teeth which engage upon a plurality of radial aligned gear teeth of a pinion gear. The radial aligned gear teeth of the pinion gear mate into the adjacent gear teeth of the linear gear rack such that the linear motion of the diaphragm element translates through the linear gear rack causing a corresponding rotation of the pinion gear. An indicator needle is associated with the pinion gear such that the movement of the needle through the linear gear rack link to the diaphragm element can be read upon overlaid calibrated measurement indicia. Generally, the indicator needle and the pinion gear rotate about an axis normal to the linear range of the linear gear rack. A biasing spring within the device acts upon the linear gear rack and the indicating needle associated pinion to provide a zero-state reading and provide resistance to movement of the indicator until energy is imparted by a ventilation equipment triggered respiration event.

The overlaid calibrated measurement indicia of the pressure measuring manometer may be provided by a transparent or translucent cover affixed to the pressure chamber. The calibrated indicia is imparted on the cover in a durable fashion as may be created through printing, embossing, engraving, or other appropriate means and are in alignment for ready interpretation of the indicating needle relative to the indicia. In a preferred embodiment, the cover has a semicircular orientation with a viewing structure perpendicular to the pressure chamber. The viewing structure is comprised of one or more viewing windows on its side or top surfaces, wherein the measurement indicia may be viewed through any one or more of the viewing windows.

A further embodiment of the present invention includes an integrated alarm affixed to the pressure measuring manometer. The alarm is mechanically coupled to the pinion gear and is triggered by cessation of the pinion gear moving after a predetermined length of time. The alarm utilizes an internal power source and can create an alert through visual and/or auditory mechanisms. The alarm itself is contained in a casing configured to be attached directly to the manometer device with a rod-like axle that extends out of the casing, through a co-pending portal in the manometer and into the pinion gear assembly of the manometer. As the pinion gear oscillates in response to changes in pressure within the pressure chamber, the then affixed rod-like axle also is placed in motion. A sensing means is coupled to the rod-like axle within the alarm casing such that motion of the assembly can be determined and an alarm condition triggered when appropriate, such as a protracted period of inaction in the pinion gear.

Other features and advantages of the present invention will become readily apparent from the following detailed description, the accompanying drawings, and the appended claims.

BRIEF SUMMARY OF THE FIGURES

The invention will be more easily understood by a detailed explanation of the invention including drawings. Accordingly, drawings which are particularly suited for explaining the inventions are attached herewith; however, it should be understood that such drawings are for descriptive purposes only and as thus are not necessarily to scale beyond the measurements provided. The drawings are briefly described as follows.

DETAILED DESCRIPTION

While the present invention is susceptible of embodiment in various forms, there is shown in the drawings and will hereinafter be described a presently preferred embodiment of the invention, with the understanding that the present disclosure is to be considered as an exemplification of the invention, and is not intended to limit the invention to the specific embodiment illustrated.

Figure 1:
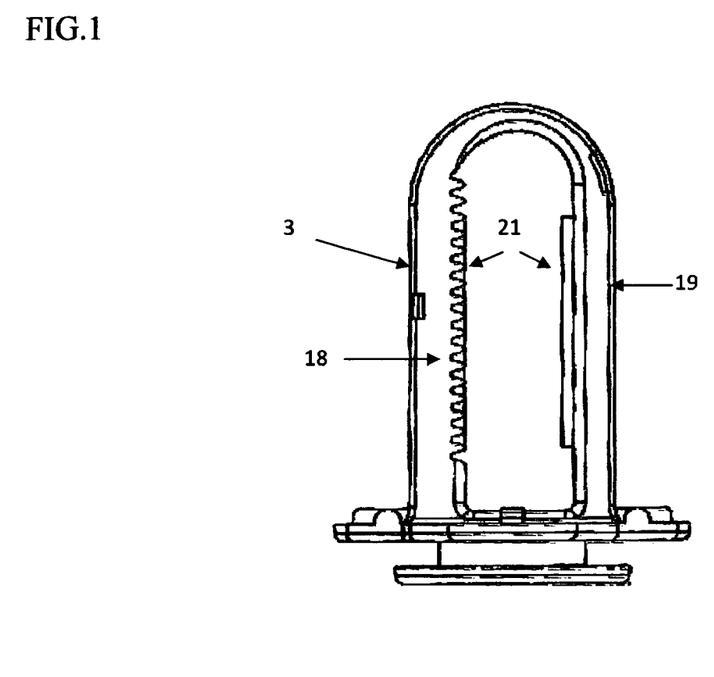
FIG. 1 is a side view of a linear gear rack with alignment spur.
Figure 2:
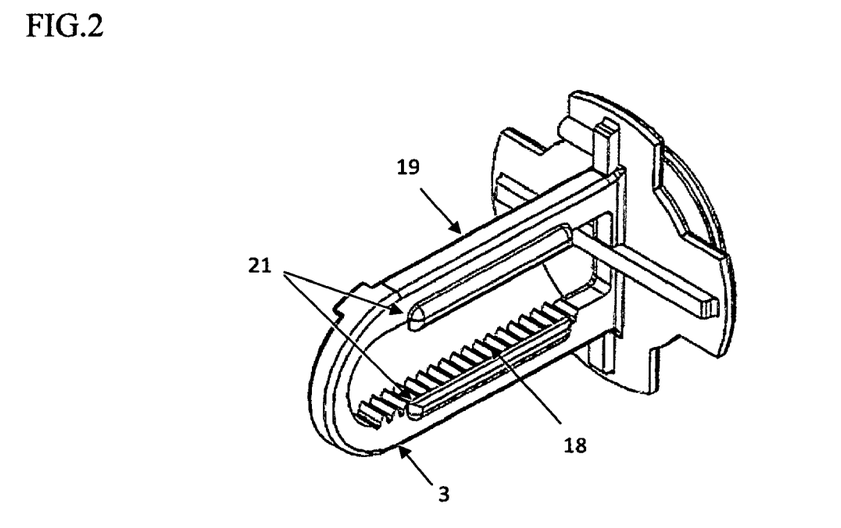
FIG. 2 is a perspective view of a linear gear rack with alignment spur.

Referring more specifically to the figures, FIG. 1 and FIG. 2 show the linear gear rack of the present invention. Linear gear rack 3 further includes an alignment spur 19. The criticality of alignment spur 19 will be further described below relative to performance of the linear gear rack/alignment spur assembly in a pressure measuring manometer.

Figure 3:
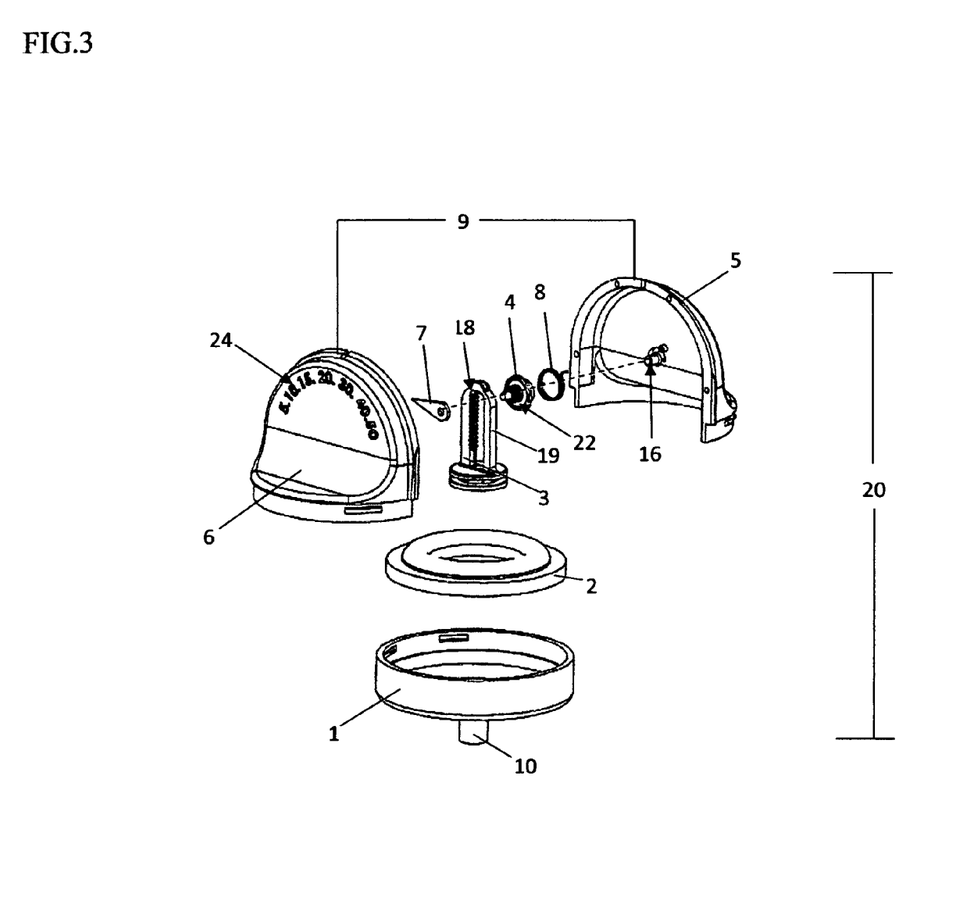
FIG. 3 is an exploded view of a first embodiment manometer in accordance with the present invention wherein the linear gear rack includes an alignment spur, the translucent cover has a viewing window in the side face and the biasing spring is of a torsion type relative to a pinion gear.
Figure 4:
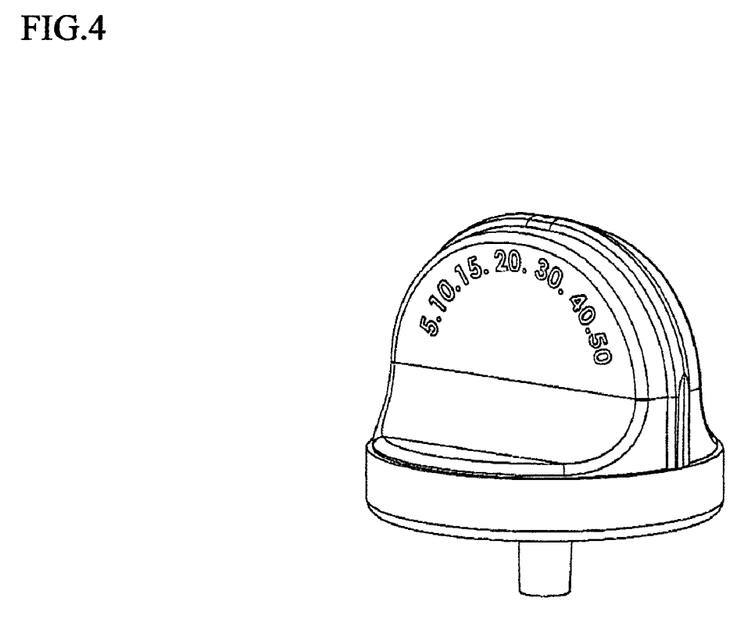
FIG. 4 is a perspective view of a first embodiment manometer.
Figure 5:
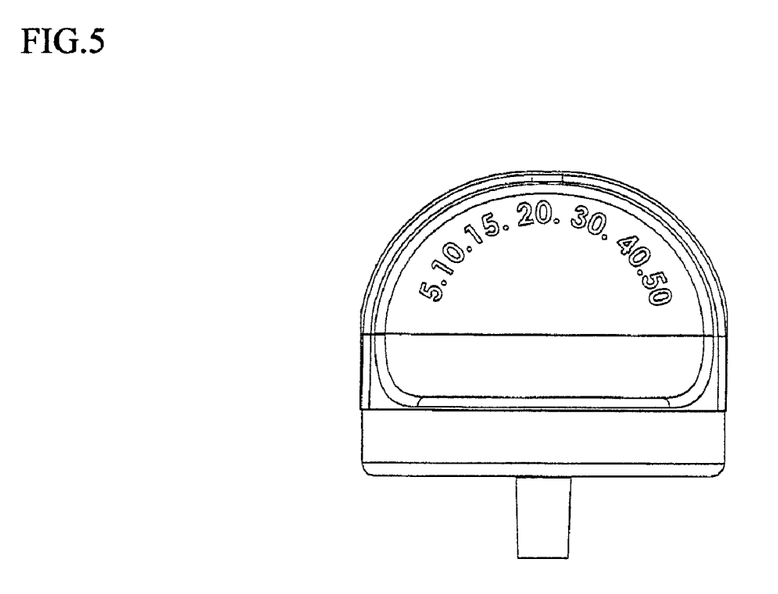
FIG. 5 is a side view of a first embodiment manometer.
Figure 6:
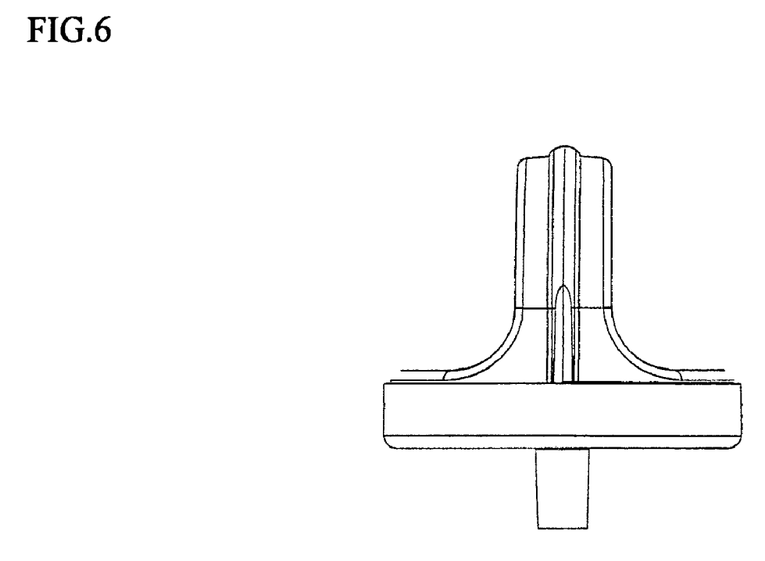
FIG. 6 is an end view of a first embodiment manometer.
Figure 7:
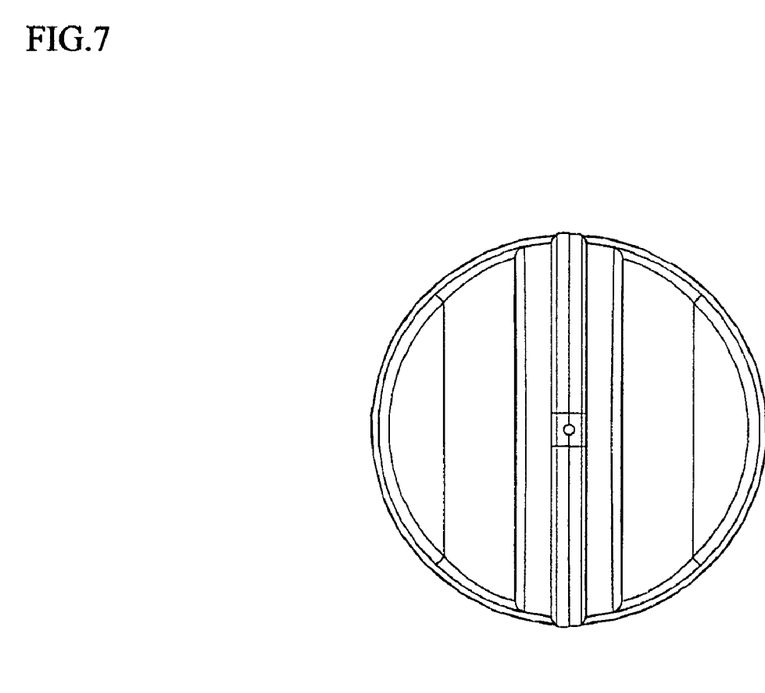
FIG. 7 is a top view of a first embodiment manometer.

For illustrative purposes the present invention is provided in a preferred embodiment by the device generally shown in FIG. 3. The manometer 20 comprises pressure chamber 1 attached to diaphragm element 2 and capped with cover unit 9. Diaphragm element 2 is placed into pressure chamber 1 such that an airtight seal is created between the pieces. Cover unit 9 is pervious to the ambient fluidic pressure and engages the pressure chamber 1 to maintain the air tight seal between the pressure chamber 1 and the diaphragm element 2. Within pressure chamber 1, there is an air inlet port 10, through which the closed or otherwise constrained test environment of interest is accessed. A representation of how such an air inlet port might be used in shown in FIG. 16 whereby air inlet port 10 is affixed to a respiratory ventilation system.

Diaphragm element 2 provides an interface between the pressure associated with pressure chamber 1 and the open fluidic ambient pressure provided through the cover unit 9. Linear gear rack 3 is attached to diaphragm element 2 at a center point of the overall diaphragm element. In a preferred embodiment the center point of diaphragm element 2 is durably strong so as to provide positive engagement of the linear gear rack 3.

Alignment spur 19 is of critical performance in insuring uniform center engagement and translation of linear force into linear gear rack 3 by diaphragm element 2. The alignment spur 19 is directly opposed to a long orientation defined by linear gear rack 3 and is spaced apart by a gap essentially equal to a space required for fitment of pinion gear 4. The alignment spur 19 acts upon pinion gear 4 by maintaining close relationship of the linear gear rack and the needle associated pinion gear, thus providing improved resolution of small pressure changes and increased accuracy of measurement as the measuring device operates through a cycling period. Alignment spur 19 and pinion gear 4 are separated by gap 23 of between 0.001 of an inch and 85% of the height of an individual gear tooth of pinion gear 4, wherein said gap 23 is measured at a point directly opposite where at least one of said plurality of adjacent aligned gear teeth of said linear gear rack engage upon at least one of said plurality of radial aligned gear teeth of said pinion gear. Alignment spur 19 may further include one or more position supports 21 (shown in FIG. 1 and FIG. 2) that extend from alignment spur 19 and/or linear gear rack 3 so as to prevent sideways slip of the linear gear rack 3 and pinion gear 4 by extending at least partially along a side aspect of pinion gear 4.

Torque induced upon linear gear rack 3 by deflection of diaphragm element 2 is a significant issue as this force will cause deleterious off-center angling and corresponding restriction of movement of linear gear rack 3. Such angling and restriction of movement of linear gear rack 3 will hinder the ability of pinion gear 4 to rotate about its axis, thus compromising manometer performance and usefulness. Prior art attempts to overcome such torque include the use of counteracting weights positioned opposite a linear gear rack, such as taught in U.S. Published Patent Application No. 20060118123 to Quinn et al, hereby incorporated by reference. Such counterweight systems to oppose torque induced by the linear rack system are contraindicated for use in a system exposed to a repetitive cycling such as encountered with a patient's respiration. The first issue in a counterweight type system is that the linear rack gear measurement assembly has a resulting higher mass, a mass which in turn must be overcome by the energy pulse created by change in the pressure chamber. In the event the energy pulse is small due to low pressure changes, the energy pulse may be insufficient to overcome the mass of the system and thus prevent the pressure change from being indicated. A further issue with the higher mass of a counterweight system is that created by the resulting momentum imparted within the measurement assembly when the energy pulse is sufficient to overcome the static moment. As the measurement assembly is put in motion by a sufficiently high energy pulse, and that energy pulse then stops, the momentum of the measurement assembly continues in the direction by which it was first set in motion. The continued motion caused by the momentum within the measurement assembly will be reflected by the system as an overrun in the reflected pressure measurement indicated and a resulting increased loss of precision and accuracy. The use of an alignment spur 19 in the present invention acts to overcome the off-center torque of the linear gear rack, insuring continuous alignment registration of the motive components and is as a result the pressure measurement manometer is typically and reliably capable of measuring diaphragm element deflections of as little as 0.03 inch.

Pinion gear 4 is positioned within the linear gear rack 3 such that pinion gear teeth 22 and linear gear rack gear teeth 18 are directly engaged such that movement of linear gear rack 3 is translated to rotational movement of pinion gear 4. The resolution or accuracy of the pressure reading is set by the number of linear gear teeth 18 and pinion gear teeth 22 and is typically and reliably capable of measuring deflections of as little as 0.03 inch when using conventional plastic injection fabrication technology for production of the geared components. Typical height of an individual gear tooth comprising linear gear rack gear teeth 18 or pinion gear teeth from either linear gear rack 3 and pinion gear 4 will be scaled according to the desired dimension of the overall pressure measuring manometer 20, with gear height of 0.024 inch to 0.030" inch being representative of a manometer having a diameter of about 1.3 inches. The number of gear teeth 22 associated with pinion gear 4 are generally within the range of 16 and 28 teeth per 360° rotation of the pinion gear when used in a pressure measuring manometer of about 1.3 inch diameter. The number of teeth 22 may be increased or decreased based upon the respective increase or decrease of the diameter measure of the intended manometer.

Pinion gear 4 has affixed thereto an associated indicator needle 7. Indicator needle 7 may be affixed by any suitable means that afford long term durability and resistance to loss, such as by adhesive attachment, thermal welding, or mechanical engagement. The indicator needle 7 will move in an arc defined by the degree of rotation of the associated pinion gear 4. The degree of rotation in the measurement arc is typically less than or equal to 360°, preferably less than or equal to 270°, and most preferably less than or equal to 180°. Acting upon pinion gear 4 is a biasing spring in the form of a torsion spring 8. Torsion spring 8 aids in centering the overall measurement assembly of pinion gear 4, indicator needle 7, dual rack stirrup 3 and diaphragm element 2 at a zero-state corresponding to the pressure in the pressure chamber 1 and the ambient temperature being equal to one another. Torsion spring 8 and pinion gear 4 are mounted onto support post 16 presented on cover unit back 5 so that the elements may freely rotate on support post 16 without undue friction.

The cover unit 9 is comprised of back cover unit 5 and front cover unit 6. In a preferred embodiment, cover unit 9 has a semicircular orientation with a viewing structure perpendicular to the pressure chamber. Cover unit 9 engages into pressure chamber 1, preferably by snapping into a fixed and durable arrangement. One or more measurement indicia 24 are overlaid in the transparent viewing windows provided in cover unit 9 for interpreting the positional relationship between indicator needle 7 and measure indicia 24. Measurement indicia 24 will indicate a scale relative to pressure changes to be determined for a system and will typically have an upper useful range of 60 cm-water. The measurement indicia 24 are imparted on the cover in a calibrated and durable fashion as may be created through printing, embossing, engraving, or other appropriate means and are in alignment for ready interpretation of the indicating needle relative to the indicia.

Practical application of the manometer represented by FIG. 3 on determining a patient's respiratory (inhalation/exhalation) pressure is of the following operational model:

Step 1—Affix manometer to ventilation system using air inlet port 10, apply ventilation system to patient Step 2—As patient initiates inhalation phase, pressure builds in pressure chamber 1

Step 3—Increase in pressure chamber 1 versus ambient pressure causes deflection of diaphragm element 2

Step 4—Deflection of diaphragm element 2 causes linear gear rack 3 to move in a corresponding incremental linear direction against biasing spring 8

Step 5—Linear displacement of linear gear rack 3 translates to rotational movement of pinion gear 4 through engaged gear teeth 18 and 22, respectively Step 6—Rotation of pinion gear 4 corresponds to a similar sweep of the associated indicator needle 7

Step 7—As indicator needle 7 sweeps through an arc limited by the degree of rotation by pinion gear 4, the indicator needle 7 is viewed through front cover unit 6 and a measure is taken relative to measurement indicia 24 dependent upon the point where indicator needle 7 stops its sweep and begins to move in the opposite direction due to the combined end of patient exhalation and action of biasing spring 8

Figure 8:
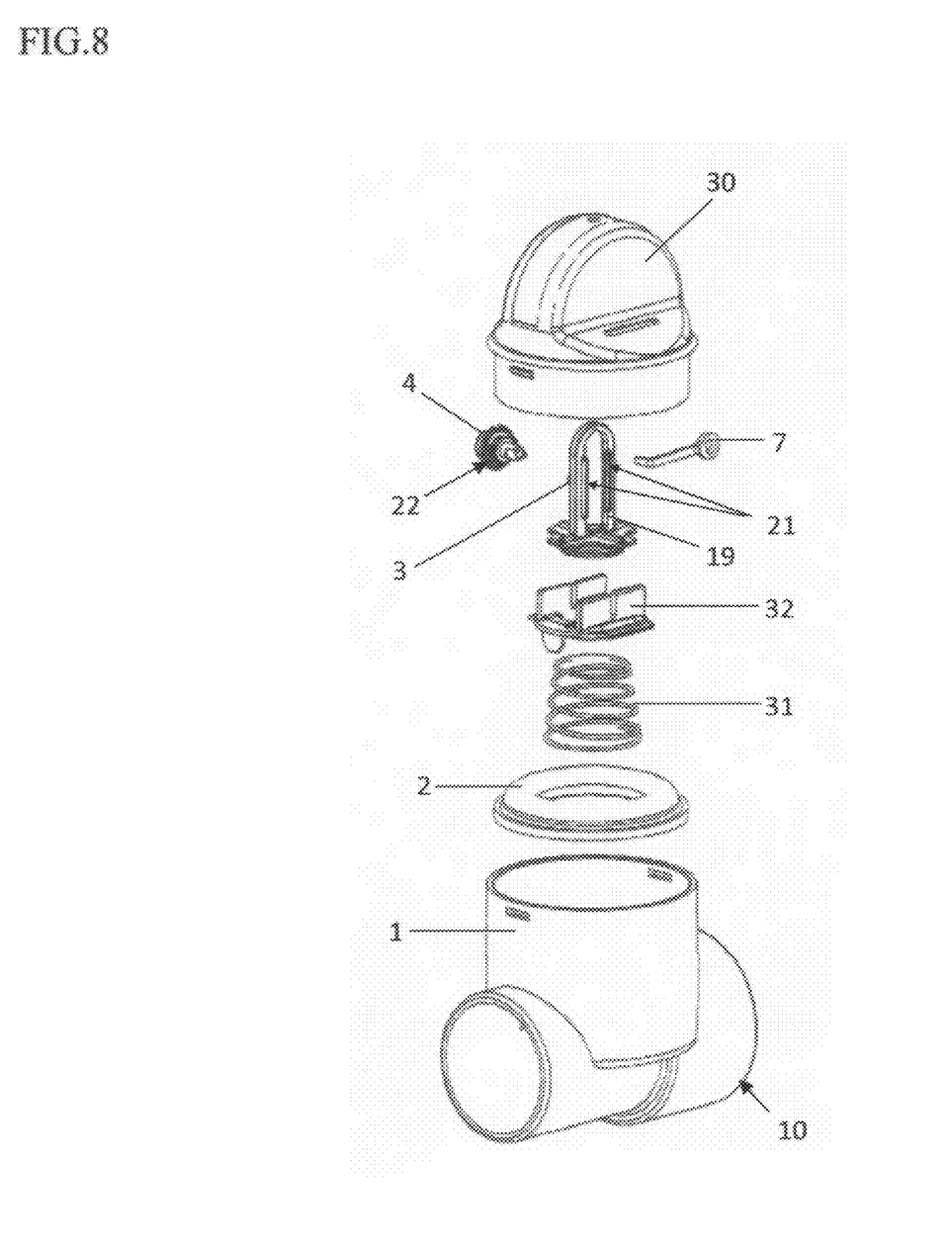
FIG. 8 is an exploded view of a second embodiment manometer in accordance with the present invention wherein the linear gear rack includes an alignment spur, the translucent cover has a viewing window in the top arc face and the biasing spring is of a compression type relative to the diaphragm element.
Figure 9:
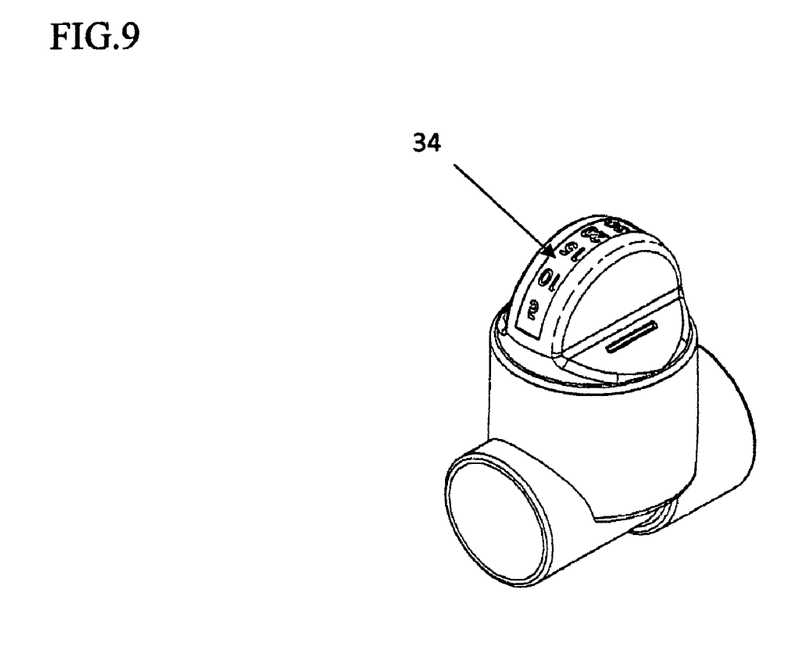
FIG. 9 is a perspective view of a second embodiment manometer.
Figure 10:
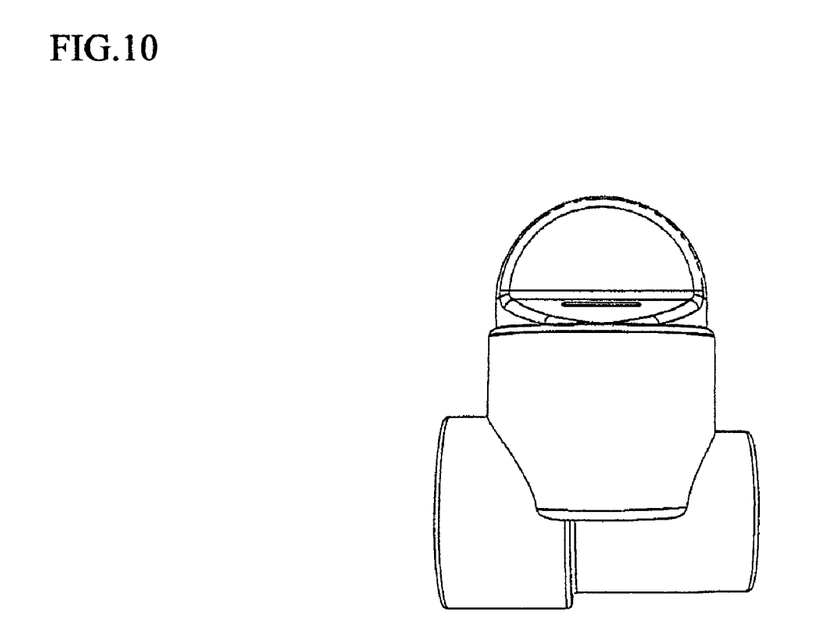
FIG. 10 is a side view of a second embodiment manometer.
Figure 11:
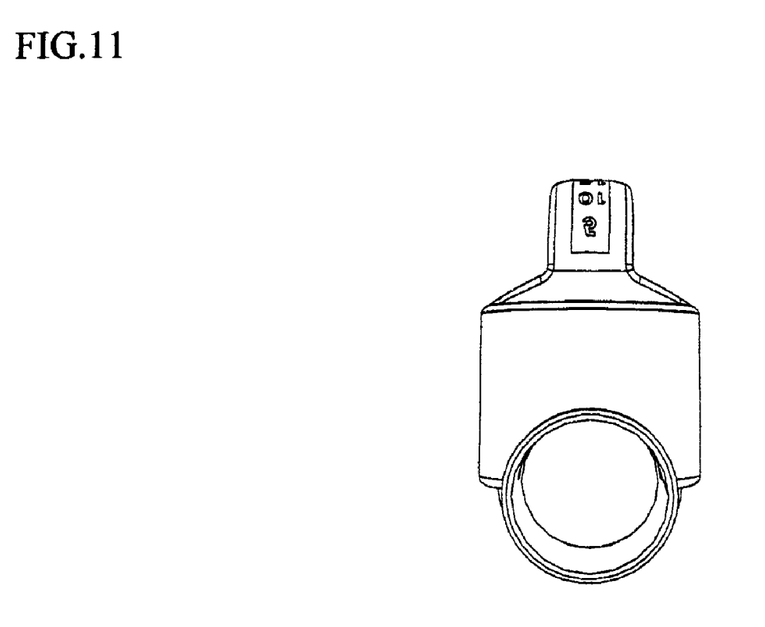
FIG. 11 is an end view of a second embodiment manometer.
Figure 12:
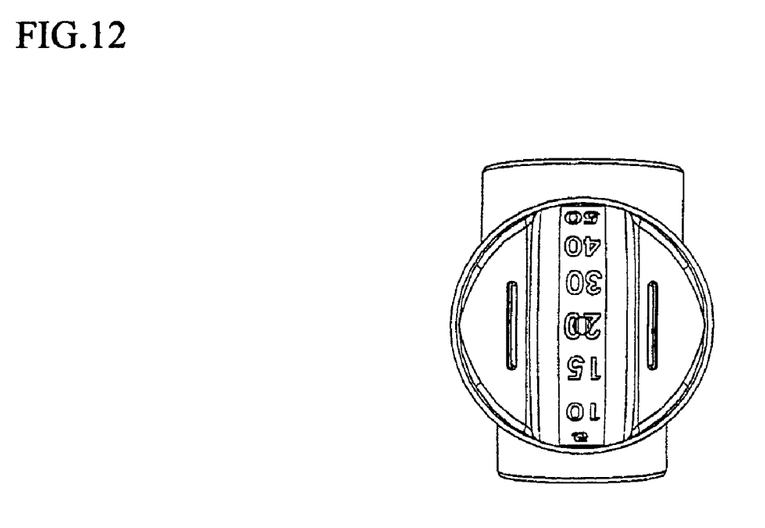
FIG. 12 is a top view of a second embodiment manometer.

FIG. 8 is an alternate manometer design within the scope of the present invention. In lieu of a two piece cover unit, a single cover unit 30 is employed. Single cover unit 30 has at least one transparent viewing window through which to indicator needle 7 may be viewed. As The transparent viewing window has at least one set of measurement indicia 34 presented on the top arc and/or upon either viewing face (see FIG. 9). In the invent both a top arc and side face viewing window are employed, indicator needle 7 may include an angled bend at the point where an interior side face transitions to an interior top arc face within the cover unit 30 so as to allow for precision reading of the indicator needle 7 location through its sweep through multiple simultaneous viewing perspectives. A support cradle 32 is used to maintain the pinion gear 4 and linear gear rack 3/alignment spur 19 assembly in an oriented relationship. A linear compression spring 31 is used as a biasing means and acts to provide zero-state pressure measurement in manometer by acting upon diaphragm element 2.

The various components and pieces used in the construction of the pressure measuring manometer of the present invention hereforeto described may be composed of a number of suitable materials. Preferred compositions include thermoplastics and thermoset polymers, which may include performance altering and/or aesthetic modifying additives, and when used in a medical environment are generally radio-transparent so as to not interfere with diagnostic visualizing equipment and be resistant to degradation by standard sanitization procedures. Particularly preferred for use in the construction of the pressure chamber and the cover units includes polymer compositions having an optical clarity index as measured by percent light transmittance per ASTM D1003 of at least 85%, as exemplified by polystyrenes, acrylics, K-resin and polycarbonates. The manometer components which are in motion, such as the linear gear rack, the pinion gear, the alignment spur, and the indicator needle are composed of low surface energy and/or lubricous polymer compositions such as nylons, acetal, polyolefins and specifically DELRIN and polyethylene which are resistant to structural failure or excessive wear induced by cyclic repetition. Diaphragm element 2 is composed of an extensible material, and preferably an elastic material having a minimum extensibility of 110% such as silicone, butyl rubber, natural rubber, latex, and the like. Biasing springs such as torsion spring 8 or compression spring 31 are preferably fabricated from materials that are non-magnetic so as to not interfere with high magnetic fields as are encountered in diagnostic equipment such a Magnetic Resonance Imaging (MRI). Particularly preferred composition for the biasing springs includes stainless steel.

Figure 13:
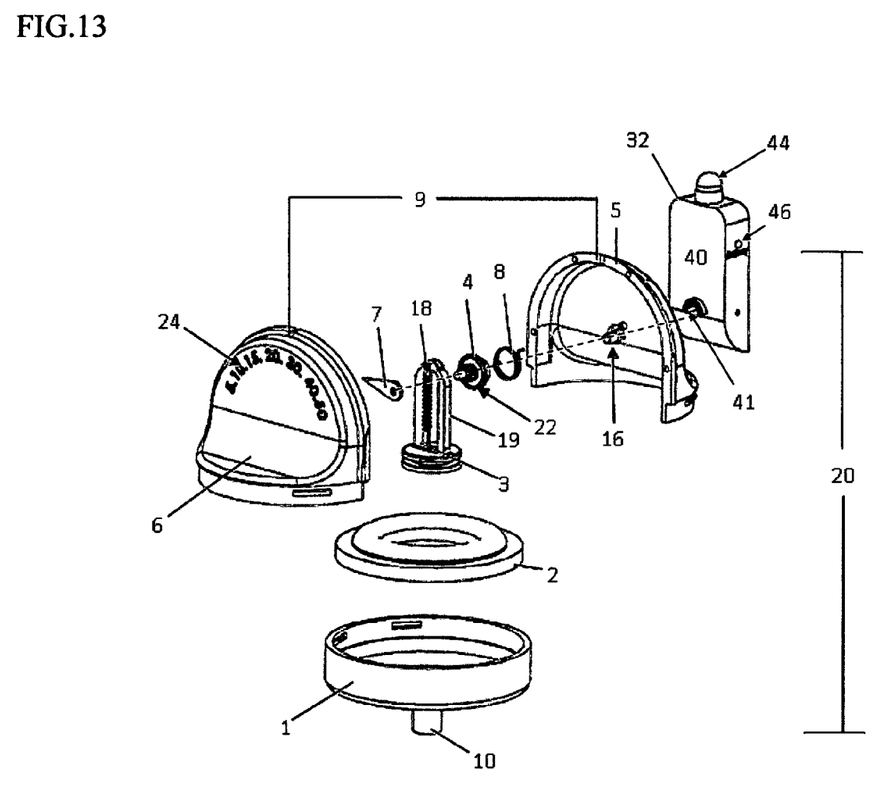
FIG. 13 is an exploded view of a first embodiment manometer in accordance with the present invention wherein the linear gear rack includes an alignment spur, the translucent cover has a viewing window in the side face, the biasing spring is of a torsion type relative to a pinion gear and an integrated apnea alarm is affixed to the back of the top cover.
Figure 14:
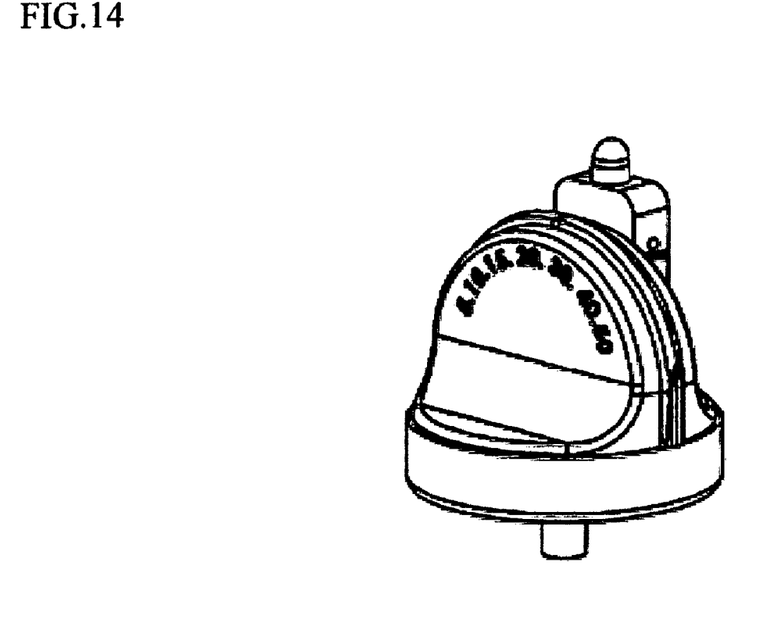
FIG. 14 is a perspective view of a first embodiment manometer including an affixed integrated apnea alarm.
Figure 15:
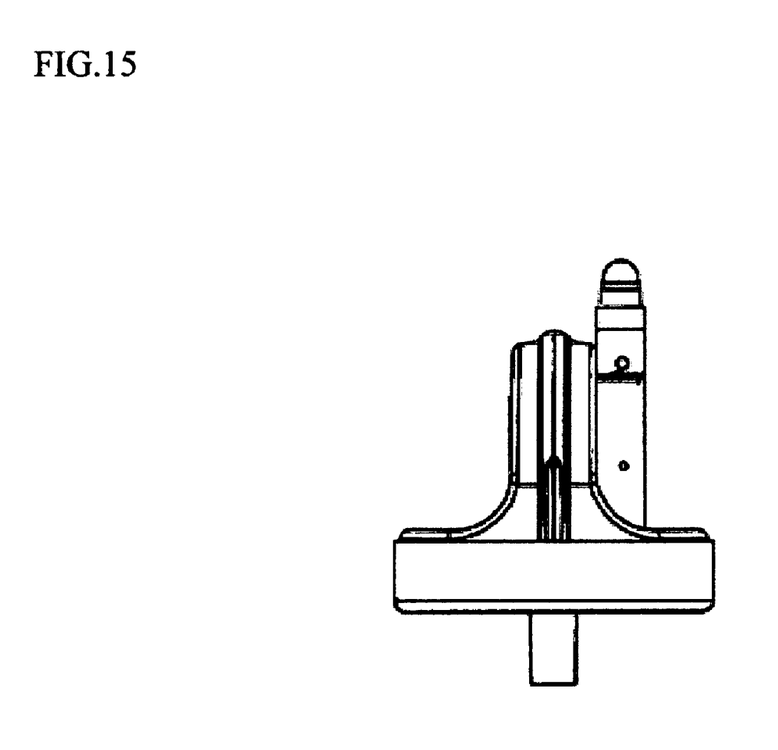
FIG. 15 is an end view of a first embodiment manometer including an affixed integrated apnea alarm.

In reference to FIG. 13, therein is disclosed a further embodiment of a pressure measuring manometer 20 wherein an apnea alarm 40 affixed. The alarm is configured to be attached to the back cover unit 5 and includes a rod-like extension or axle 41 that extends through the alarm case 32 and back cover unit 5 to interconnect with pinion gear 4. As pinion gear 4 rotates, axle 41 rotates an equivalent amount. Axle 41 is connected to a sensor within alarm case 32. The sensor may include any suitable type as is know in the art for determining rotational movement of an axle. In the event that the sensor registers failure of axle 41 to rotate for a protracted time period, whether due to cessation of breathing by the patient or failure of the ventilation system to operate, an alarm condition is triggered. Contained with the alarm case is a self-contained power source such as a battery. The battery is in part a power source for the axle rotation sensing means and further provides energy for the visual and/or auditory alerts triggered by the alarm condition. Suitable visual alerts include light emitting diodes (LED) 44 of various attention attracting colors, which may either blink or remain in a continuous-on state depending the alarm condition. Auditory alerts may include single or multiple tones, which may either pulse or remain in a continuous-on state depending upon the alarm condition. A further status LED 46 can be incorporated in the battery powered circuit to show an alarm ready state and/or battery charge condition.

Figure 16:
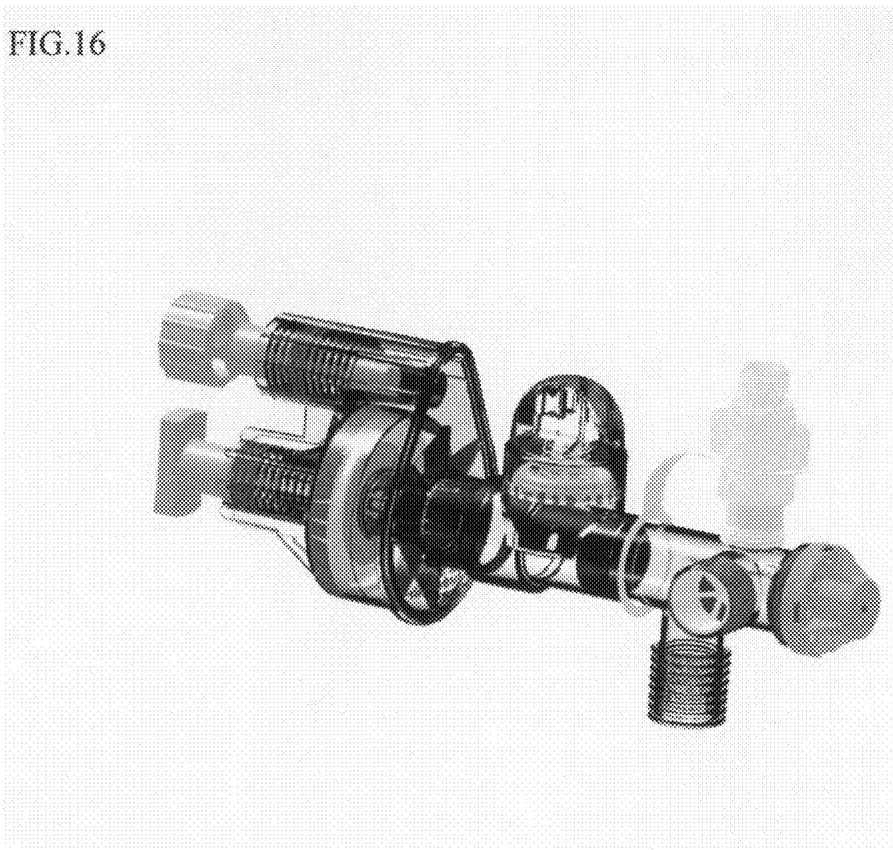
FIG. 16 is a front view of a second embodiment pressure measuring manometer combined with a representative ventilation system.

A representative combined device of a pressure measure manometer 20 and an alarm 40 is shown attached to a respiratory ventilation system in FIG. 16 wherein the ventilator system is exemplified by a VORTRAN AUTOMATIC RESUSCITATOR 40 (VAR trademark of Vortran Medical Technology 1 of Sacramento, Calif.). In the representative application of the pressure measuring manometer and alarm is for indicating the condition of the proximal airway pressure of a patient.

EXAMPLE

A pressure measuring manometer in accordance with the present invention, and specifically in accordance with the embodiment depicted in FIG. 8, was fabricated and tested for performance.

Component Construction in Example:
Top Cover
    Base Diameter: 1.27 inch
    Total Height: 1.20 inch
    Composition: K-Resin
Pressure Chamber
    Total Length: 1.85 inch
    Inlet Port Diameter: 1.05 inch
    Top Cover Fitment Diameter: 1.28 inch
    Composition: K-Resin
Diaphragm Element
    Diameter: 1.27 inch
    Deflection Element Thickness: 0.040 inch
    Composition: Silicon
Biasing Spring
    Type: Compression
    Composition: Stainless steel
    Wire Diameter: 0.024 inch
    Pitch: 0.131 inch
    Active Coils: 3.3
    Load Capacity: 0.24 pound force at 0.21 inch compression
Pinion Gear
    Diameter: 0.30 inch
    Gear Teeth: 19 teeth in 360°
    Individual gear tooth width: 0.027 inch
    Individual gear tooth width: 0.024 inch
    Composition: Acetal
Linear Gear Rack
    Total geared rack length: 0.74 inch
    Individual gear tooth width: 0.030 inch
    Individual gear tooth width: 0.024 inch
    Composition: Acetal
Alignment Spur
    Composition: Acetal
    Spacing from Linear Gear Rack: 0.032 inch Example Performance:

| | Measured Pressure (cm-water) | | | | | | | |
|---|---|---|---|---|---|---|---|---|
| | 5.0 | 10.0 | 15.0 | 20.0 | 30.0 | 40.0 | 50.0 | 60.0 |
| Linear Rack Movement (inch) | 0.02 | 0.04 | 0.07 | 0.09 | 0.12 | 0.15 | 0.19 | 0.21 |

From the foregoing, it will be observed that numerous modifications and variations can be affected without departing from the true spirit and scope of the novel concept of the present invention. It is to be understood that no limitation with respect to the specific embodiments illustrated herein is intended or should be inferred. The disclosure is intended to cover, by the appended claims, all such modifications as fall within the scope of the claims.

The invention claimed is:

1. A pressure measuring manometer comprising:
   a. a pressure chamber fluidly connected to a test environment;
   b. a diaphragm element;
   c. a linear gear rack comprising a plurality of adjacent aligned gear teeth and an alignment spur
   d. a pinion gear comprising a plurality of radial aligned gear teeth;
   e. an indicator needle;
   f. a cover unit with at least one viewing window and having at least one set of calibrated pressure measurement indicia thereupon;
   wherein at least one of said plurality of adjacent aligned gear teeth of said linear gear rack engage upon at least one of said plurality of radial aligned gear teeth of said pinion gear;
   wherein said alignment spur is in close proximity of said pinion gear at a point directly opposite whereby at least one of said plurality of adjacent aligned gear teeth of said linear gear rack engage upon at least one of said plurality of radial aligned gear teeth of said pinion gear;
   wherein said alignment spur acts upon said pinion gear to maintain said pinion gear teeth and linear gear rack teeth is close engagement;
   wherein said diaphragm element is adjacent to said pressure chamber and is connected to said linear gear rack;
   wherein said indicator needle is attached to said pinion gear;
   whereupon a change in pressure in a test environment induces a change of pressure in said pressure chamber and thereby causes deflection of said diaphragm element;
   wherein said deflection of diaphragm element causes linear movement of said linear gear rack which is translated into rotation of said pinion gear and of said indicator needle;
   wherein position of the indicator needle is viewable through at least one viewing window of said cover unit and said calibrated measurement indicia;
   wherein said pressure measurement of the said test environment is determined by correspondence of said indicator needle with said calibrated measurement indicia; and
   wherein linear movements of 0.03 inch or greater are measured.

2. A pressure measuring manometer as in claim 1, wherein said pressure measuring manometer further comprises a biasing spring.

3. A pressure measuring manometer comprising:
   a. a pressure chamber fluidly connected to a test environment;
   b. a diaphragm element;
   c. a linear gear rack comprising a plurality of adjacent aligned gear teeth and an alignment spur
   d. a pinion gear comprising a plurality of radial aligned gear teeth;
   e. an indicator needle;
   f. a cover unit with at least one viewing window and having at least one set of calibrated pressure measurement indicia thereupon;
   wherein at least one of said plurality of adjacent aligned gear teeth of said linear gear rack engage upon at least one of said plurality of radial aligned gear teeth of said pinion gear;
   wherein said alignment spur is in close proximity of said pinion gear at a point directly opposite whereby at least one of said plurality of adjacent aligned gear teeth of said linear gear rack engage upon at least one of said plurality of radial aligned gear teeth of said pinion gear;
   wherein said alignment spur acts upon said pinion gear to maintain said pinion gear teeth and linear gear rack teeth is close engagement;
   wherein said diaphragm element is adjacent to said pressure chamber and is connected to said linear gear rack;
   wherein said indicator needle is attached to said pinion gear;
   whereupon a change in pressure in a test environment induces a change of pressure in said pressure chamber and thereby causes deflection of said diaphragm element;
   wherein said deflection of diaphragm element causes linear movement of said linear near rack which is translated into rotation of said pinion gear and of said indicator needle;
   wherein position of the indicator needle is viewable through at least one viewing window of said cover unit and said calibrated measurement indicia;
   wherein said pressure measurement of the said test environment is determined by correspondence of said indicator needle with said calibrated measurement indicia; and
   wherein said pressure measuring manometer measures pressure cyclic changes in a respiratory system of a human patient, wherein the cyclic changes for at least 3000 consecutive cycles.

4. A pressure measuring manometer for use in a patient respiration measurement, comprising:
   a. a pressure chamber fluidly connected to a patient respiratory ventilation system;
   b. a diaphragm element;
   c. a linear gear rack comprising a plurality of adjacent aligned gear teeth and an alignment spur
   d. a pinion gear comprising a plurality of radial aligned gear teeth;
   e. an indicator needle;
   f. a cover unit with at least one viewing window and having at least one set of calibrated pressure measurement indicia thereupon;
   wherein at least one of said plurality of adjacent aligned gear teeth of said linear gear rack engage upon at least one of said plurality of radial aligned gear teeth of said pinion gear;
   wherein said alignment spur is in close proximity of said pinion gear at a point directly opposite whereby at least one of said plurality of adjacent aligned gear teeth of said linear gear rack engage upon at least one of said plurality of radial aligned gear teeth of said pinion gear;
   wherein said alignment spur acts upon said pinion gear to maintain said pinion gear teeth and linear gear rack teeth is close engagement;

wherein said diaphragm element is adjacent to said pressure chamber and is connected to said linear gear rack;

wherein said indicator needle is attached to said pinion gear;

whereupon a change in pressure in a test environment induces a change of pressure in said pressure chamber and thereby causes deflection of said diaphragm element;

wherein said deflection of diaphragm element causes linear movement of said linear gear rack which is translated into rotation of said pinion gear and of said indicator needle;

wherein position of the indicator needle is viewable through at least one viewing window of said cover unit and said calibrated measurement indicia;

wherein said pressure measurement of the said test environment is determined by correspondence of said indicator needle with said calibrated measurement indicia;

wherein the resolution of linear movement in the linear gear rack is at least 0.03 inch and the pressure measuring manometer is capable of operating at least 10 cycles per minute for a continuous period of at least 3000 cycles.

* * * * *